United States Patent [19]

Komori et al.

[11] Patent Number: 4,844,898
[45] Date of Patent: Jul. 4, 1989

[54] WOUND-HEALING PREPARATIONS

[75] Inventors: Seiichi Komori, Fuchu; Toyojiro Muramatsu, Shizuoka, both of Japan

[73] Assignees: Kowa Co., Ltd., Nagoya; Teika Seiyaku Co., Ltd., Toyama, both of Japan

[21] Appl. No.: 81,150

[22] Filed: Aug. 4, 1987

[30] Foreign Application Priority Data

Sep. 2, 1986 [JP] Japan .................................. 61-206312

[51] Int. Cl.$^4$ ............................................ A01N 59/12
[52] U.S. Cl. .................................................. 424/150
[58] Field of Search .......................................... 424/150

[56] References Cited

U.S. PATENT DOCUMENTS

| 2,826,532 | 3/1958 | Hosmer | 424/150 X |
| 3,911,107 | 10/1975 | Krezanoski | 424/150 X |
| 4,401,651 | 8/1983 | Knutson | 424/150 X |

Primary Examiner—Ellis P. Robinson
Assistant Examiner—Leon R. Horne
Attorney, Agent, or Firm—Oblon, Spivak, McClelland, Maier & Neustadt

[57] ABSTRACT

A wound-healing preparation is composed of 50–90 wt. % of a sugar, 0.5–10 wt. % of povidone-iodine, and 1–20 wt. % of water. A buffer is also contained in an amount sufficient to adjust the pH of the preparation to 3.5–6. Preferably, the preparation may additionally contain 0.1–5 wt. % of an agent for imparting an appropriate consistency and stability, which is selected from polysaccharides and derivatives thereof.

9 Claims, 1 Drawing Sheet

WOUND-HEALING PREPARATIONS

BACKGROUND OF THE INVENTION (i) Field of the Invention:

This invention relates to stable external medicinal preparations useful for the healing of damaged skin (hereinafter abbreviated as "wounds" for the sake of brevity) such as burns, decubitus and open wounds. More specifically, it is concerned with wound-healing preparations which contain a sugar and povidone-iodine (polyvinylpyrrolidone-iodine complex) as effective ingredients.

(ii) Description of the Prior Art:

Sugars such as honey and molasses have conventionally been used, as folk therapy, for the treatment of burns and open wounds. These sugars have also been known to have bacteriostatic action and granulation tissue growth-promoting effects. Povidone-iodine is a drug employed extremely widely as an antiseptic throughout the world.

It has recently been reported that excellent wound-healing effects were achieved when granulated sugar was mixed with povidone-iodine preparations such as "Betadine" (trade mark of The Purdue Frederick Co., Norwalk, Connecticut, U.S.A.) ointment, "Betadine" solution and "Isodine Gel" (trade mark; product of Meiji Seika Kaisha, Ltd., Tokyo, Japan) and the resultant mixtures were applied to various wounds [R.A. Knutson et al., "Southern Medical Journal", 74(11), 1329–1335 (1981); and Kiyokazu Sone et al., "Byoin Yakugaku (Hospital Pharmacology)", 10(5), 315–322 (1984)].

Further, Japanese Patent Application Laid-Open No. 141409/1980 of Nov. 5, 1980, which corresponds in part to U.S. Pat. No. 4,401,651 issued on Aug. 30, 1983, discloses a composition composed of 20 parts by weight of granulated sugar, 5 parts by weight of "Betadine" ointment and 2 parts by weight of "Betadine" solution. Although "Betadine" ointment and solution are povidone-iodine preparations produced and marketed in U.S.A. by The Purdue Frederick Co., they are not commercially available in Japan. Details of their ingredients are hence unknown to the present inventors.

The following problems were however found on compositions, which had been prepared respectively by mixing commercial povidone-iodine preparations available to the present inventors with a sugar in accordance with the formulation described in Japanese Patent Application Laid-Open No. 141409/1980 referred to above.

(1) The content of povidone-iodine in each of the commercial povidone-iodine preparations was not constant. The ratio of the sugar to povidone-iodine in the resulting composition hence varied from one production lot to another, whereby it was difficult to obtain compositions of uniform quality.

(2) The mixture of each of the commercial povidone-iodine preparation and the sugar has an extremely high viscosity. A special apparatus was therefore needed to perform uniform kneading. Furthermore, it was difficult to produce the composition in a large volume by a single mixing operation.

(3) When stored at room temperature, each of the compositions separated into two layers or was rendered like starch syrup and moreover, its effective ingredient underwent decomposition to reduce the drug efficacy. It was thus necessary to store the compositions in a cool and dark place. The effective ingredient was however decomposed in several months even when stored in the above manner. It was hence essential to prepare the compositions before use.

Among these problems, the problem (3) which requires the preparation of a composition before use is an extremely serious problem. The problem (3) has therefore led to such inevitable drawbacks that the composition cannot be prepared except for large hospitals equipped, for example, with the above-mentioned kneader, aseptic manipulation facilities, sterilization equipment and the like and patients must attend hospitals whenever administration is required.

SUMMARY OF THE INVENTION

An object of this invention is to provide a wound-healing preparation which can be formulated with a uniform composition by a simple operation and moreover, can be stored stably over a long period of time.

The present inventors have thus carried out an extensive investigation to achieve the above object of this invention. As a result, it has been found that a stable preparation, which has overcome the above-described problems, can be obtained by using povidone-iodine in place of such a povidone-iodine preparation, mixing povidone-iodine, a sugar and water at a predetermined ratio and adjusting the pH of the resultant mixture to a specific level with a buffer. The present inventors have also found that an incorporation of a polysaccharide or its derivative as an agent for imparting an appropriate consistency and stability in the above stable preparation can provides a more stable preparation which does not undergo phase separation even when stored over a long period of time.

In one aspect of this invention, there is thus provided a wound-healing preparation which comprises 50–90 wt.% of a sugar, 0.5–10 wt.% of povidone-iodine, 1–20 wt.% of water and a buffer in an amount sufficient to adjust the pH of the preparation to 3.5–6.

In another aspect of this invention, there is also provided a wound-healing preparation which comprises 50–90 wt.% of a sugar, 0.5–10 wt.% of povidone-iodine, 1–20 wt.% of water, 0.1–5 wt.% of an agent for imparting an appropriate consistency and stability selected from polysaccharides and derivatives thereof, and a buffer in an amount sufficient to adjust the pH of the preparation to 3.5–6.

The preparation of this invention is extremely easy to produce and is stable over a long period of time. It can thus be filled in opaque containers for practical use.

BRIEF DESCRIPTION OF THE DRAWING

The above and other objects, features and advantages of the present invention will become apparent from the following description and the appended claims, taken in conjunction with the accompanying sole drawing, FIG. 1, which diagrammatically illustrates the relationship between the stability of aqueous solutions of povidone-iodine and a sugar and their pH.

DETAILED DESCRIPTION OF THE INVENTION AND PREFERRED EMBODIMENTS

Figure 1:
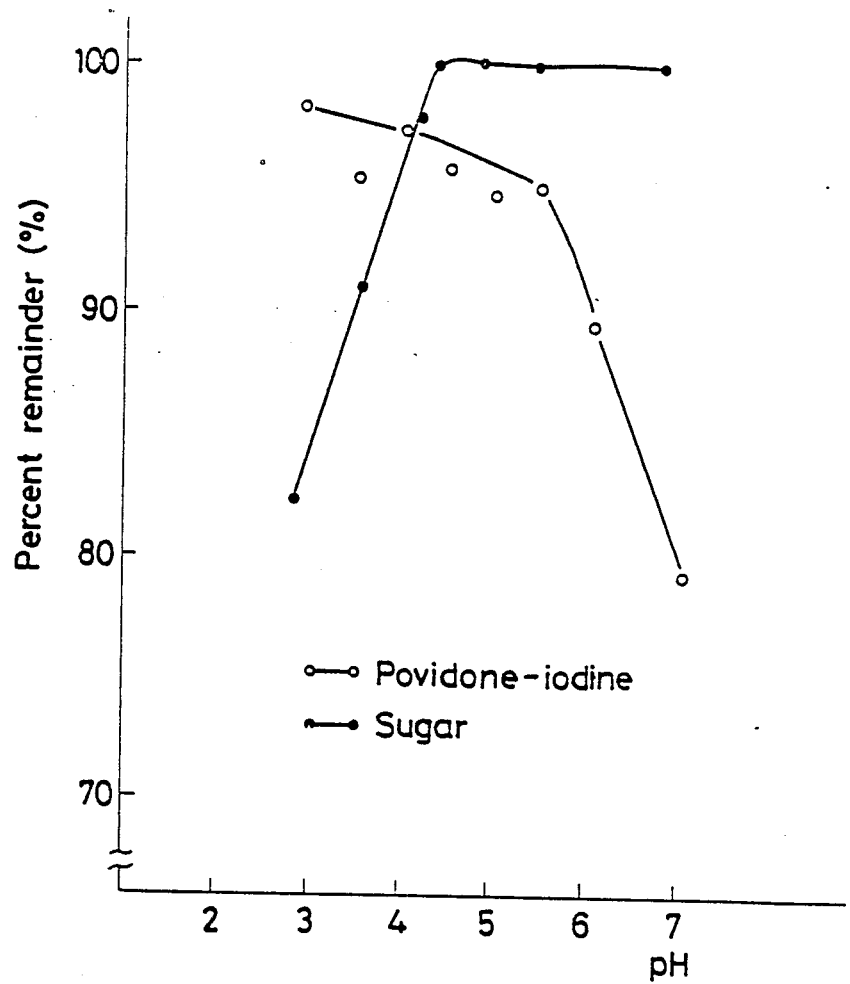

The sugar, which is to be used in this invention, must be a non-reducing sugar. Sucrose, glucose, dextrose, honey, molasses, etc may be mentioned by way of example. Among these, sucrose and purified sucrose specified in The Japan Pharmacopoeia are particularly preferred in order to obtain compositions of uniform quality. On the other hand, it is possible to use, as povidone-iodine, that described in the Standard for Quasi-Drug Ingredients, The Japan Pharmacopoeia.

The proportion of the sugar is 50–90 wt.% (hereinafter referred to merely by "%") of the whole composition with 60–80% being preferred. The proportion of povidone-iodine ranges from 0.5%, the minimum proportion requires for the exhibition of bacteriostatic action, to 10%. Water is added in an amount of 1–20% with 1–15% being preferred.

As illustrative examples of the polysaccharide or its derivative which is an agent for imparting an appropriate consistency and stability, dextrin, gum arabic, pullulan, chondroitin sulfate, methylcellulose, sodium carboxymethylcellulose an the like may be mentioned. These polysaccharides and their derivatives show specific effects for the stability of the preparation. Other agents which are also employed generally for the same purpose cannot achieve sufficient effects or on the contrary, give some deleterious effects to the stability. Such an agent may preferably be added in an amount of 0.1–5%, notably, 0.1–3% based on the whole composition.

In addition to these essential ingredients, it is also possible to incorporate a routine excipient and a povidone-iodine solubilizer as needed. Illustrative examples of the solubilizer may include potassium iodide, sodium iodide, glycerin and the like. As exemplary excipients, may be mentioned glycols such as polyethylene glycol 400, 1500, 4000 and 6000, polyoxyethylene polyoxypropylene glycol and polypropylene glycol; glycerins such as glycerin and polyglycerin; polyoxyethylene-hardened castor oil; polyoxyethylene polyoxypropylene block polymer; etc.

When the preparation of this invention is added with the above-described ingredients only, its effective ingredients, i.e., the sugar and povidone-iodine are instable. It is hence necessary to adjust its pH. Namely, a composition consisting of 80% of granulated sugar, 3% of povidone-iodine and 17% of water was prepared. Using a 0.1 M disodium phosphate-citrate buffer, portions of the composition were adjusted to various pH levels respectively. They were stored at 40° C. for 2 weeks. The percentages of the sugar remaining in the respective samples were measured by high performance chromatography, while the percentages of povidone-iodine remaining in the respective samples were measured by titration. Results are diagrammatically illustrated in FIG. 1. As apparent from the above experiment, it is within a range of pH 3.5–pH 6 that the sugar and povidone-iodine are both stable.

As a buffer capable of adjusting the pH of the preparation of this invention to such a level, may be mentioned by way of example a lactate buffer, citrate buffer, phosphate buffer, potassium hydrogenphthalate buffer or the like.

No particular limitation is imposed on the production method of the preparation of this invention. For example, it may be produced by dissolving povidone-iodine and a solubilizer therefor in a buffer, adding and mixing an aqueous solution of a sugar either alone or together with an aqueous solution of an agent for imparting an appropriate consistency and stability, both solutions having been prepared separately, and optionally adding an excipient to adjust the viscosity.

Having generally described the invention, a more complete understanding can be obtained by reference to certain specific examples, which are provided herein for purposes of illustration only and are not intended to be limiting unless otherwise specified.

EXAMPLES

The present invention will hereinafter be described by the following Examples.

EXAMPLE 1

|   |   | parts by weight |
|---|---|---|
| (1) | Povidone-iodine | 3 |
| (2) | 0.1 M lactic acid-sodium lactate buffer (pH 5.5) | 11 |
| (3) | Potassium iodide | 0.9 |
| (4) | Purified sucrose | 70.7 |
| (5) | 1 N sodium hydroxide solution | 1.2 |
| (6) | Polyethylene glycol 400 | 9 |
| (7) | Polyethylene glycol 6000 | 2.6 |
| (8) | Polyoxyethylene polyoxypropylene glycol | 1 |
| (9) | Glycerin | 0.6 |

To a solution of the ingredients (1) and (3) dissolved in the ingredient (2), the ingredients (5) and (4) were added and mixed. A mixture of the ingredients (6), (7), (8) and (9), which had been prepared separately, was added gradually to the former mixture so that all the ingredients were kneaded into a homogeneous preparation.

Test 1:

The invention product prepared in Example 1, Hospital Formulation I ["Gekkan Yakuji (The Pharmaceuticals Monthly)", 25(7), 97 (1983)] and Hospital Formulation II ["Gekkan Yakuji (The Pharmaceuticals Monthly)", 25(5), 129 (1983)], the latter two being conventional products, were heated to 60° C. to measure pH variations and the percentages of available iodine and sugar remaining therein. Results are summarized in Tables 1–3.

| Hospital Formulation I: | |
|---|---|
| Granulated sugar | 72.4% |
| Isodine Gel | 21.0 |
| Isodine Solution | 6.6 |
| Hospital Formulation II: | |
| Granulated sugar | 57.1% |
| Simple syrup | 17.2 |
| Isodine Gel | 25.7 |

TABLE 1

| (pH) | | | |
|---|---|---|---|
| | Invention product | Hospital Formulation I | Hospital Formulation II |
| Initial | 5.14 | 4.20 | 4.12 |
| 3 Days later | 4.27 | 3.57 | 2.78 |
| 6 Days later | 4.18 | 2.68 | 2.53 |
| 9 Days later | 4.16 | 2.67 | 2.68 |

TABLE 2

| (Available Iodine, %) | | | |
|---|---|---|---|
| | Invention product | Hospital Formulation I | Hospital Formulation II |
| Initial | 100 | 100 | 100 |

TABLE 2-continued

| | (Available Iodine, %) | | |
|---|---|---|---|
| | Invention product | Hospital Formulation I | Hospital Formulation II |
| 3 Days later | 94.6 | 96.9 | 61.0 |
| 6 Days later | 93.4 | 30.1 | 0 |
| 9 Days later | 91.4 | 0 | 0 |

TABLE 3

| | (Sugar, %) | | |
|---|---|---|---|
| | Invention product | Hospital Formulation I | Hospital Formulation II |
| Initial | 100 | 100 | 100 |
| 3 Days later | 100.7 | 91.5 | 40.8 |
| 6 Days later | 98.5 | 25.2 | 5.5 |
| 9 Days later | 97.7 | 5.5 | 0 |

EXAMPLE 2

A preparation of the following composition was formulated in the same manner as in Example 1.

| | parts by weight |
|---|---|
| Povidone-iodine | 3 |
| 0.1 M citrate buffer (pH 5.3) | 11 |
| Potassium iodide | 0.9 |
| Purified sucrose | 65 |
| 1 N sodium hydroxide | 1 |
| Polyethylene glycol 400 | 8 |
| Polyethylene glycol 1500 | 7.3 |
| Polyoxyethylene polyoxypropylene glycol | 2.8 |
| Glycerin | 1 |

EXAMPLE 3

| | | parts by weight |
|---|---|---|
| (1) | Povidone-iodine | 3 |
| (2) | 0.05 M citrate buffer (pH 5.3) | 8.9 |
| (3) | Potassium iodide | 0.7 |
| (4) | Purified sucrose | 70 |
| (5) | Agent for imparting an appropriate consistency and stability | 0.5 |
| (6) | 1 N sodium hydroxide | 0.8 |
| (7) | Polyethylene glycol 400 | 14 |
| (8) | Polyoxyethylene polyoxypropylene glycol | 1.1 |
| (9) | Glycerin | 1.0 |

To a solution of the ingredients (1) and (3) dissolved in the ingredient (2), the ingredients (6) and (4) were added and mixed. A mixture of the ingredients (5), (7), (8) and (9), which had been prepared separately, was added gradually to the former mixture, so that all the ingredients were kneaded into a homogeneous preparation.

Test 2:

After the preparations formulated in Example 3 with different agents (5) shown below in Table 4 were stored at 40° C. for 3 months, the percentages of available iodine and sugar remaining in the respective preparations were measured and the consistency of the preparations were also observed. Results are summarized in Table 4.

TABLE 4

| Agent for imparting appropriate consistency and stability | Percent remainder of available iodine (%) | Percent remainder of sugar (%) | Consistency (appearance) |
|---|---|---|---|
| Invention preparation | | | |
| Pullulan | 92 | 98 | Unchanged |
| Dextrin | 86 | 98 | " |
| Gum arabic | 87 | 100 | " |
| Chondroitin sulfate | 82 | 100 | " |
| Methylcellulose | 82 | 97 | " |
| Sodium carboxymethylcellulose | 85 | 98 | " |
| Avicel (trade mark) | 81 | 97 | " |
| Comparative preparation | | | |
| Albumin | 60 | 80 | " |
| Sodium casein | 55 | 80 | " |
| Gelatin | 65 | 90 | " |
| Poly(sodium acrylate) | 48 | 96 | Rubbery |

EXAMPLE 4

| | | parts by weight |
|---|---|---|
| (1) | Povidone-iodine | 3 |
| (2) | 0.1 M lactic acid-sodium lactate buffer (pH 5.5) | 11.0 |
| (3) | Potassium iodide | 0.9 |
| (4) | Purified sucrose | 70.7 |
| (5) | Pullulan | 0.6 |
| (6) | 1 N sodium hydroxide solution | 1.2 |
| (7) | Polyethylene glycol 400 | 9 |
| (8) | Polyethylene glycol 6000 | 2 |
| (9) | Polyoxyethylene polyoxypropylene glycol | 1 |
| (10) | Glycerin | 0.6 |

To a solution of the ingredients (1) and (3) dissolved in the ingredient (2), the ingredients (6) and (4) were added and mixed. A mixture of the ingredients (5), (7), (8), (9) and (10), which had been prepared separately, was added gradually to the former mixture, so that all the ingredients were kneaded into a homogeneous preparation.

Having now fully described the invention, it will be apparent to one of ordinary skill in the art that many changes and modifications can be made thereto without departing from the spirit and scope of the invention as set forth herein.

We claim:

1. A wound-healing preparation, comprising: 50-90 wt.% of a sugar, 0.5-10 wt.% of povidone-iodine, 1-20 wt.% of water and a buffer selected from the group consisting of lactate buffer, citrate buffer, phosphate buffer and potassium hydrogen phthalate buffer in an amount sufficient to adjust the pH of the preparation to 3.5-6.

2. The wound-healing preparation of claim 1, which preparation further comprises from 0.1 to 5 wt% of an agent which imparts consistency and stability to the preparation, said agent being a polysaccharide or derivative thereof.

3. The wound-healing preparation of claim 1, wherein the amount of said sugar ingredient present ranges from 60-80% by weight.

4. The wound-healing preparation of claim 1, wherein the amount of said water in the composition ranges from 1-15% by weight.

5. The wound-healing preparation of claim 2, wherein said polysaccharide or derivative thereof is dextrin, gum arabic, pullulan, chondroitin sulfate, methylcellulose or sodium carboxymethylcellulose.

6. The wound-healing preparation of claim 2, wherein the amount of said polysaccharide or derivative thereof in the composition ranges from 0.1 to 3 wt.%.

7. The wound-healing preparation of claim 2, wherein said composition contains a solubilizing ingredient which is potassium iodide, sodium iodide or glycerin.

8. The wound-healing preparation of claim 2, wherein said composition further comprises at least one excipient which is a glycol, a glycerin, polyoxyethylene-hardened castor oil or polyoxyethylene-polyoxypropylene block polymer.

9. The wound-healing preparation of claim 1, wherein said sugar is a non-reducing sugar selected from the group consisting of sucrose, glucose, dextrose, honey and molasses.

* * * * *